United States Patent
Monster et al.

(10) Patent No.: US 9,149,053 B2
(45) Date of Patent: Oct. 6, 2015

(54) METHOD FOR PRODUCING CONJUGATED LINOLEIC ACID

(75) Inventors: Jeroen Monster, Wormerveer (NL); Youchun Yan, Wormerveer (NL)

(73) Assignee: STEPAN SPECIALTY PRODUCTS LLC, Wilmington, DE (US)

( * ) Notice: Subject to any disclaimer, the term of this patent is extended or adjusted under 35 U.S.C. 154(b) by 0 days.

(21) Appl. No.: 13/976,734

(22) PCT Filed: Dec. 21, 2011

(86) PCT No.: PCT/EP2011/073681
§ 371 (c)(1),
(2), (4) Date: Dec. 16, 2013

(87) PCT Pub. No.: WO2012/089598
PCT Pub. Date: Jul. 5, 2012

(65) Prior Publication Data
US 2014/0113968 A1  Apr. 24, 2014

(30) Foreign Application Priority Data
Dec. 31, 2010 (CN) .......................... 2010 1 0623322

(51) Int. Cl.
*A61K 31/201* (2006.01)
*A23D 7/04* (2006.01)
*C11C 1/00* (2006.01)
*C11C 3/14* (2006.01)

(52) U.S. Cl.
CPC .............. *A23D 7/04* (2013.01); *A61K 31/201* (2013.01); *C11C 1/005* (2013.01); *C11C 1/007* (2013.01); *C11C 3/14* (2013.01)

(58) Field of Classification Search
CPC ........................................................ A23D 7/04
See application file for complete search history.

(56) References Cited

U.S. PATENT DOCUMENTS

| | | | |
|---|---|---|---|
| 2,744,125 A | 5/1956 | Meeks et al. | |
| 2,895,976 A | 7/1959 | Stepas et al. | |
| 6,420,577 B1 * | 7/2002 | Reaney et al. | ................ 554/126 |
| 2002/0032233 A1 * | 3/2002 | Saebo et al. | ................ 514/549 |

FOREIGN PATENT DOCUMENTS

| | | |
|---|---|---|
| CN | 102229527 | 11/2011 |
| EP | 902082 | 3/1999 |
| EP | 1493801 | 1/2005 |
| EP | 1712609 | 10/2006 |
| EP | 1801193 | 6/2007 |
| EP | 2332901 | 6/2011 |
| WO | WO 9718320 | 5/1997 |
| WO | WO 2007118614 | 10/2007 |

OTHER PUBLICATIONS

Weiss et al., J Am Chem Soc, 1967, vol. 44, pp. 146A to 148A.
Tasan et al., Eur Food Res Technol, (2005), 220: 251 to 254.
Watanabe et al, Journal of Oleo Science, vol. 55, No. 10, 537-543 (2006).
Uehara H. et al., "A Novel Method for Solvent Fractionation of Two CLA Isomers," Journal of the Am Oil Chemists' Soc, vol. 83, No. 3 pp. 261-267, 2006.
International Preliminary Report on Patentability from PCT/EP2011/073681 dated Jul. 2, 2013.
International Search Report from PCT/EP2011/073681 dated May 24, 2012.

* cited by examiner

*Primary Examiner* — Yong Chu
*Assistant Examiner* — Ana Z Muresan
(74) *Attorney, Agent, or Firm* — Barnes & Thornburg LLP

(57) ABSTRACT

A method for producing a composition comprising conjugated linoleic acid in an amount of at least 55% by weight, comprises: (i) providing a liquid mixture comprising, as the free acids, from 50 to 95% by weight conjugated linoleic acid and at least 5% by weight of saturated C12-C22 fatty acids; (ii) cooling the liquid mixture to a temperature at which at least a part of the saturated C12-C22 fatty acids precipitate from the mixture as a solid; and (iii) separating the solid from the liquid, wherein the liquid obtained in (iii) comprises conjugated linoleic acid in an amount of at least 55% by weight.

19 Claims, No Drawings

METHOD FOR PRODUCING CONJUGATED LINOLEIC ACID

CROSS REFERENCE TO RELATED APPLICATIONS

This application is a U.S. nationalization under 35 U.S.C. §371 of International Application No. PCT/EP2011/073681, filed Dec. 21, 2011, which claims priority to Chinese Patent Application No. 201010623322.3, filed Dec. 31, 2010. The disclosers set forth in the referenced applications are incorporated herein by reference in their entireties.

This invention relates to a method for producing conjugated linoleic acid (CLA).

Conjugated isomers of long chain polyunsaturated fatty acids are known to have potential benefits, for example when used in food products. Examples of such acids include the isomers of conjugated linoleic acid (CLA); typically, the cis 9, trans 11 ("c9,t11") and trans 10, cis 12 ("t10,c12") isomers are the most abundantly present isomers in CLA, and they are generally present in a 1:1 weight ratio when synthesised chemically. Conjugated isomers can be produced from the corresponding non-conjugated fatty acids, usually by isomerisation in the presence of a base.

EP-A-0902082 discloses a process for the preparation of materials comprising mainly conjugated isomers of long chain polyunsaturated fatty acids wherein an oil or a free fatty acid composition or an alkyl ester composition thereof, containing at least 25 wt % of at least one isomer other than the conjugated isomers of long chain polyunsaturated fatty acids, is subjected to a treatment with a base in a solvent and wherein the solvent is an alcohol with at least 3 C-atoms and at least two hydroxyl groups having: a ratio of number of C-atoms: number of OH groups of at least 1.25 but less than 3.5, preferably from 1.5 to 2.75, while the reaction is carried out between 100 and 180° C., more preferably between 120 and 180° C.

EP-A-1493801 discloses a process for producing a conjugated di- or poly- unsaturated fatty acid having from 12 to 24 carbon atoms, or a salt or ester thereof, which comprises reacting a non-conjugated free fatty acid, or a salt or ester thereof, with a base in the presence of a solvent comprising a monohydric alcohol having from 1 to 6 carbon atoms, wherein the reaction is carried out at a temperature of from 120° C. to 200° C. in the presence of water in an amount of at least 4% by weight based on alcohol.

A process for producing CLA is also disclosed in copending applications CN 200910249088.X and EP10250232.5.

The products that are produced in the processes described above contain CLA together with other fatty acids that originate from the starting oils. Typically, the CLA is not separated from these other fatty acids that are present prior to its use. However, there is a need for CLA products that contain relatively high levels of CLA. Although the processes described in EP-A-1493801, CN 200910249088.X and EP10250232.5 do allow the production of a product containing a relatively high amount of CLA, there can still be a need to reduce the saturated fatty acid (SAFA) content of the products and/or to increase the CLA content of the product to even higher levels.

The fractionation of glyceride oils by cooling or "winterization" is described, for example, in Weiss et al, J Am Chem Soc, April 1967, volume 44, pages 146A-148A and is mentioned in Tasan et al, Eur Food Res Technol, (2005), 220: 251-254.

Watanabe et al, Journal of Oleo Science, volume 55, number, 10, 537-543 (2006) discloses that the monoglyceride of CLA can be purified from the free fatty acid of CLA and glycerol by winterization in hexane. The authors were concerned solely with increasing the purity of the monoglyceride in which the free acid was present as an impurity.

WO 2007/118614 describes the separation of the cis9, trans11 and trans10, cis12 isomers of CLA by crystallisation of the free acids.

The conventional method for increasing the CLA free acid content of a composition is by short path distillation. However, distillation methods of this type are costly and involve harsh temperature conditions that can damage the product.

Surprisingly, a much simpler, less harsh and more cost effective method for increasing the level of CLA in CLA-containing compositions has now been found.

According to the invention, there is provided a method for producing a composition comprising conjugated linoleic acid (CLA) in an amount of at least 55% by weight, comprising:
(i) providing a liquid mixture comprising, as the free acids, from 50 to 95% by weight CLA and at least 5% by weight of saturated C12-C22 fatty acids;
(ii) cooling the liquid mixture to a temperature at which at least a part of the saturated C12-C22 fatty acids (SAFA) precipitate from the mixture as a solid; and
(iii) separating the solid from the liquid,
wherein the liquid obtained in (iii) comprises CLA in an amount of at least 55% by weight. All of the percentages are based on the total C12-C22 fatty acids present in the respective composition, liquid mixture or liquid.

Unexpectedly, the separation of SAFA from CLA as free fatty acids can be achieved according to the invention. The solid precipitate (usually crystalline) comprising SAFA that is obtained in (ii) is of a very suitable particle size for separation in (iii) from the liquid that is depleted in SAFA and enriched in CLA. Moreover, at levels of 50-95% by weight of CLA and at least 5% by weight of SAFA based on the total C12-C22 fatty acids present, when the fatty acids are in the form of free acids rather than glycerides, it is surprising that it is the SAFA that preferentially precipitates.

The liquid mixture comprises, as the free acids, from 50 to 95% by weight CLA and at least 5% by weight, preferably from 5 to 25% by weight, more preferably from 5 to 15% by weight, of saturated C12-C22 fatty acids (SAFA), based on the total C12-C22 fatty acids present. If the amount of CLA in the liquid mixture exceeds 95% by weight based on the total C12-C22 fatty acids present, then the CLA will also precipitate from the mixture on cooling. This means that the SAFA cannot be effectively separated from the CLA.

The term liquid mixture refers to the CLA-containing substance in (i), which is a liquid at 20° C. and in step (i) of the method of the invention. It will be appreciated that the liquid mixture will not be a liquid at all temperatures.

The liquid mixture typically comprises, in addition to the CLA and the SAFA, unsaturated C12-C22 fatty acids such as oleic acid, as well as polyunsaturated fatty acids other than CLA. These monounsaturated and polyunsaturated fatty acids make up the balance of the fatty acids present to 100% and together the fatty acids preferably constitute the major part (greater than 90%, such as greater than 95%, by weight) of the liquid mixture.

It will be understood that the term "fatty acids", as used herein, means straight chain, saturated or unsaturated (including mono- and poly-unsaturated) carboxylic acids having from 12 to 22 carbon atoms.

The liquid mixture provided in part (i) of the method of the invention is preferably produced by the isomerisation of safflower oil or sunflower oil having from 5 to 15% SAFA based on the total C12-C22 fatty acids present, more preferably produced by the isomerisation of safflower oil. More preferably, the liquid mixture is produced by reacting an oil comprising linoleic acid as the free fatty acid, or a salt or ester thereof, with a base in the presence of an alcoholic solvent comprising ethanol. It is a particular advantage of this method that it may be carried out on a relatively large scale whilst producing low amounts of esters of the conjugated fatty acid. The plural term "esters" is used to reflect the fact that different isomers of the conjugated fatty acid will generally be present and, therefore, the mixture will contain different ester compounds. Typically, the mixture contains said esters, preferably ethyl esters, in an amount of from 0.01% to 2% by weight, more preferably 0.2% to 1.2% by weight, such as from 0.6% to 1.0% by weight, based on total fatty acid and esters thereof. The determination of the level of esters in the mixture can be carried out by methods known to those skilled in the art.

In step (ii) of the method of the invention, the mixture is preferably cooled to a temperature in the range of from −5 to 10° C., more preferably from −4 to 5° C., such as from −3 to 3° C. Cooling may be carried out by simply placing the mixture in a cool environment having a temperature in this range. Alternatively, the cooling of the liquid mixture can be achieved more rapidly by, for example, stirring and/or applying cold fluid to the mixture or to a container that comprises the mixture or by using a cooling spiral.

Preferably, in (ii), the mixture is held at the temperature for at least 10 hours, preferably from 20 to 500 hours, such as from 30 to 100 hours.

Step (ii) of the method of the invention is preferably carried out batchwise. For example, step (ii) may be carried out on a batch of from 100 to 2000 kg of the mixture. Typically, step (ii) is carried out with from 100 to 2000 kg of the mixture in a container having a capacity of from 100 to 2000 liters.

After the desired amount of SAFA has precipitated in (ii), the solid is removed from the liquid in step (iii). Typically, in (iii), from 60 to 90% by weight of the liquid mixture is separated as the liquid. The separation of the solid from the liquid is carried out using conventional physical separation techniques such as, for example, filtration, centrifugation, decantation or combinations thereof. Preferably, the removal of the solid from the liquid comprises decantation.

The method of the invention preferably comprises after step (iii) the further step of pressing the solid in a filter press one or more times to extract residual liquid, and subsequently combining the liquid thus obtained with the liquid obtained in (iii). This allows more of the CLA to be recovered and so increases the yield of the process.

The method of the invention optionally comprises one or more further steps, such as bleaching the composition and/or forming a mono-, di-, or tri-glyceride of the CLA in the composition.

The composition that is produced by the method of the invention, which may be the liquid obtained in (iii) or a product such as a glyceride obtained from the liquid in (iii), preferably comprises less than 8% by weight saturated C12-C22 fatty acids (SAFA), more preferably less than 7.5% by weight SAFA such as less than 7% by weight SAFA, based on the total C12-C22 fatty acids present.

The fatty acid content of the composition may be determined by FAME analysis, a technique well-known to those skilled in the art.

The composition preferably comprises more than 60% by weight, more preferably more than 75% by weight, such as more than 78% by weight CLA, based on the total C12-C22 fatty acids present. For example, the composition may comprise more than 79% by weight CLA, based on the total C12-C22 fatty acids present.

Preferably, the composition that is produced by the method of the invention comprises less than 5% by weight palmitic acid, based on the total C12-C22 fatty acids present.

In one preferred embodiment of the invention, the composition comprises less than 7% by weight saturated C12-C22 fatty acids (SAFA), less than 5% by weight palmitic acid (also included in the SAFA content), more than 79% by weight CLA and from 10-15% oleic acid, based on the total C12-C22 fatty acids present.

The CLA composition preferably comprises the cis9, trans11 and trans10,cis12 isomers as the major isomers. For example, the composition preferably comprises at least 74% by weight of the cis9, trans11 and trans10,cis12 isomers of CLA based on the total C12-C22 fatty acids present. The cis9, trans11 and trans10,cis12 isomers are preferably present in a weight ratio of from 3:2 to 2:3.

The method of the invention may produce the CLA composition in a high yield from the liquid mixture. Typically, the yield of the method is such that greater than 85% of the composition is obtained based on the weight of the liquid mixture.

The method of the invention is preferably solvent-free. This means that no solvent is added during the method. Also, the liquid mixture does not contain substantial amounts of solvent, only traces that may be left over from the process for producing the liquid mixture. For example, the liquid mixture may comprise less than 1% by weight of alcohols having from 1 to 4 carbon atoms, such as ethanol, more preferably less than 0.5% by weight and no solvent is added during the method.

The composition (or the glyceride formed from the composition) preferably contains ethyl esters of CLA in an amount of from 0.01% to 2% by weight, more preferably 0.2% to 1.2% by weight, such as from 0.6% to 1.0% by weight, based on the total C12-C22 fatty acid and salt and esters thereof.

The composition (or the glyceride formed from the composition) preferably contains relatively low amounts of dialkyl ketones (DAKs). Preferably, the composition or glyceride contains dialkyl ketones in an amount of less than 100 ppm, more preferably less than 50 ppm, even more preferably less than 25 ppm. The dialkyl ketones are typically of the formula RR'CO, wherein R and R' are the same or different and are either saturated alkyl groups or unsaturated alkenyl groups having at least one carbon-carbon double bond (preferably one or two double bonds), the alkyl and alkenyl groups containing 12 to 22 (e.g., 12 to 20), preferably 14 to 18 carbon atoms, and being branched or straight chain, preferably straight chain. The composition and the glyceride are preferably suitable for use in an edible product, more preferably they are suitable for use in a food product, a food supplement or a pharmaceutical product.

The composition or the glyceride can be used as such. Alternatively, the composition or the glyceride can be used as the starting materials for a further modification, such as enrichment in an isomer, such as the cis 9, trans 11 or the trans 10, cis 12 isomer of conjugated linoleic acid. For example, the composition may be used as the starting material for a process for enriching a mixture containing different conjugated isomers of the same long chain polyunsaturated fatty acid in one of the isomers, as described in WO 97/18320, the contents of which are incorporated herein by reference.

The composition or the glyceride may be used in a food product, food supplement or pharmaceutical product. The composition or the glyceride are optionally used as a blend with a complementary fat. For example, the blend may comprise 0.3-95 wt %, preferably 2-80 wt %, most preferably 5-40 wt % of the product of the invention and 99.7-5 wt %, preferably 98-20 wt %, most preferably 95-60 wt % of a complementary fat selected from: cocoa butter, cocoa butter equivalents, palm oil or fractions thereof, palmkernel oil or fractions thereof, interesterified mixtures of said fats or fractions thereof, or liquid oils, selected from: sunflower oil, high oleic sunflower oil, soybean oil, rapeseed oil, cottonseed oil, fish oil, safflower oil, high oleic safflower oil, maize oil and MCT-oils. Food products (which term includes animal feed) contain a fat phase, wherein the fat phase contains the product of the invention. The food products are suitably selected from the group consisting of: spreads, margarines, creams, dressings, mayonnaises, ice-creams, bakery products, infant food, chocolate, confectionery, sauces, coatings, cheese and soups. Food supplements or pharmaceutical products may be in the form of capsules or other forms, suitable for enteral or parenteral application and comprise a product of the invention.

The invention will now be described with reference to the following non-limiting examples. In the examples and throughout this specification, all percentages, parts and ratios are by weight unless indicated otherwise.

EXAMPLES

Example 1

Conjugation of Safflower Oil

A 1000 liter jacketed pressure vessel is fitted with a mechanical stirrer and is provided with a connector for nitrogen. The temperature of the vessel is controlled by injecting steam or cold water in the jacket.

The materials that are used in the process are safflower oil (300 kg), base (sodium hydroxide pellets; 110 kg) and as solvent: a mixture of ethanol (280 kg) and water (20 kg).

The conjugation of the safflower oil is carried out as follows. 300 kg safflower oil is placed in the reaction vessel. 110 kg of hydroxide pellets, dissolved in the 300 kg of solvent, are added to the reaction vessel and the obtained mixture is heated to 150° C. while stirring under nitrogen. The reaction is allowed to continue for 3 hours. The mixture is cooled to 120° C. in the pressure vessel and is transferred into another vessel for removal of the ethanol.

100 kg of a saturated solution of sodium chloride in water is added to the mixture followed by stirring for 15 minutes. The layers are then allowed to separate for 30 minutes. The bottom layer is decanted.

The top layer mixture is placed into a 10% sulfuric acid solution, the bottom layer is discarded and the top layer is washed with hot water until pH 7 was reached. The washed layer is finally dried at 80° C. for 1 hour and stored under nitrogen.

Example 2

Reduction of SAFA Content in CLA Composition

A composition was produced according to the same general method as is described in Example 1.

1000 liters of the composition was filled into an intermediate bulk container (IBC) and placed in a cooling room at −3 to 3° C. with circulating air, for one month. Each day, a sample of the oil is taken and the carboxylic acid composition of the oil was analysed by FAME analysis. The FAME analysis shows the SAFA and CLA content of the oil. The temperature of the oil in the container was monitored using a data logger, which also monitored the external temperature in the cooling room.

The results are shown below.

| Time (days) | Temperature of the oil (° C.) | CLA total | CLA c9,t11 and t10,c12 | SAFA | Palmitic acid |
|---|---|---|---|---|---|
| 1 | >14 | 76.51 | 72.63 | 9.7 | 6.42 |
| 5 | 6 | 76.64 | 72.9 | 9.6 | 6.4 |
| 10 | 6 | 77.1 | 73.51 | 8.9 | 6.01 |
| 20 | 2 | 79.14 | 74.9 | 6.4 | 4.5 |
| 30 | 3 | 79.33 | 75.0 | 6.21 | 4.4 |

After 17 days in the cooling room, the external temperature of the container dropped to 0-3° C. After 1-2 days at this temperature, the crystallisation of the SAFA increases and the SAFA content of the oil decreases to less than 8% by weight of the oil. Further time at the same temperature lowers the SAFA content to below 6.5% by weight and the C16:0 (palmitic acid) content to less than 5% by weight.

Example 3

Method of Producing a Composition Comprising CLA

A composition was produced according to the same general method as is described in Example 1.

900 kg of the composition were cooled down to −3 to 3° C. for 72 hours in a container. White crystals appeared and settled down in the bottom of the container. The upper layer was decanted.

The lower layer was transferred into press filter bags and separated using a hydraulic vertical press. The pressing was repeated two times. The olein (liquid) fractions from the pressings and the upper layer are combined and pumped into a bleaching vessel for bleaching the oil.

The product thus obtained contained 79.1% by weight CLA and 6.4% SAFA and was obtained in an overall yield of 90%.

The invention claimed is:

1. A method for producing a composition comprising conjugated linoleic acid (CLA) in an amount of at least 55% by weight based on total C12-C22 fatty acids, comprising:
   (i) providing a liquid mixture comprising, as free acids, from 50 to 95% by weight conjugated linoleic acid and at least 5% by weight of saturated C12-C22 fatty acids, based on the total C12-C22 fatty acids;
   (ii) cooling the liquid mixture to a temperature at which at least a portion of the saturated C12-C22 fatty acids preferentially precipitates from the mixture as a solid; and
   (iii) separating the solid, which comprises the preferentially precipitated saturated C12-C22 fatty acids, from the liquid, which comprises the conjugated linoleic acid;
   wherein the liquid obtained in (iii) comprises conjugated linoleic acid in an amount of at least 55% by weight based on the total C12-C22 fatty acids; and
   wherein the method is solvent-free.

2. The method as claimed in claim 1, wherein the liquid mixture comprises from 5 to 15% by weight of saturated C12-C22 fatty acids based on the total C12-C22 fatty acids.

3. The method as claimed in claim 1, wherein the mixture is produced by the isomerisation of safflower oil.

4. The method as claimed in claim 1, wherein the mixture is cooled to a temperature in the range of from −5 to 10° C.

5. The method as claimed in claim 4, wherein the solid is removed from the liquid in (iii) by decantation.

6. The method as claimed in claim 5, comprising after step (iii) the further step of pressing the solid in a filter press one or more times to extract residual liquid and combining the liquid thus obtained with the liquid obtained in (iii).

7. The method as claimed in claim 4, wherein in (ii) the mixture is held at the temperature for at least 10 hours, preferably from 20 to 500 hours.

8. The method as claimed in claim 1, wherein the composition comprises less than 8% by weight saturated C12-C22 fatty acids.

9. The method as claimed in claim 8, wherein the composition comprises less than 5% by weight palmitic acid.

10. The method as claimed in claim 8, wherein the composition comprises more than 78% by weight conjugated linoleic acid.

11. The method as claimed in claim 9, wherein the yield of the process is greater than 85% based on the weight of the liquid mixture.

12. The method as claimed in claim 11, wherein in (iii) from 60 to 90% by weight of the liquid mixture is separated as the liquid.

13. The method as claimed in claim 1 further comprising bleaching the composition.

14. The method as claimed in claim 6 further comprising bleaching the composition.

15. The method as claimed in claim 1 further comprising forming a mono-, di-, or tri- glyceride of the CLA in the composition.

16. The method as claimed in claim 13 further comprising forming a mono-, di-, or tri- glyceride of the CLA in the composition.

17. The method as claimed in claim 1, wherein the CLA comprises cis9, trans11; trans10, cis12; or both the cis9, trans11 and trans10,cis12 isomers.

18. The method as claimed in claim 17, wherein the composition comprises at least 74% by weight of the cis9,trans11 and trans10,cis12 isomers of CLA based on total C12-C22 fatty acids.

19. The method as claimed in claim 17, wherein the cis9, trans11 and trans10,cis12 isomers are present in a weight ratio of 3:2 to 2:3.

\* \* \* \* \*